United States Patent
Hu et al.

(10) Patent No.: US 10,143,492 B2
(45) Date of Patent: Dec. 4, 2018

(54) HOLLOW CELIAC MINIMALLY INVASIVE SURGERY ENDOSCOPIC CHANNEL

(71) Applicant: Shanghai East Hospital, Shanghai (CN)

(72) Inventors: Hai Hu, Shanghai (CN); Kai Zhang, Shanghai (CN)

(73) Assignee: SHANGHAI EAST HOSPITAL, Shanghai (CN)

( * ) Notice: Subject to any disclaimer, the term of this patent is extended or adjusted under 35 U.S.C. 154(b) by 194 days.

(21) Appl. No.: 15/033,336

(22) PCT Filed: Dec. 15, 2014

(86) PCT No.: PCT/CN2014/093840
§ 371 (c)(1),
(2) Date: Apr. 29, 2016

(87) PCT Pub. No.: WO2015/090169
PCT Pub. Date: Jun. 25, 2015

(65) Prior Publication Data
US 2016/0278807 A1    Sep. 29, 2016

(30) Foreign Application Priority Data
Dec. 18, 2013 (CN) .......................... 2013 1 0699778

(51) Int. Cl.
*A61B 17/34* (2006.01)
*A61B 17/02* (2006.01)
*A61B 17/00* (2006.01)

(52) U.S. Cl.
CPC ...... *A61B 17/3423* (2013.01); *A61B 17/0218* (2013.01); *A61B 17/0281* (2013.01);
(Continued)

(58) Field of Classification Search
CPC . A61B 17/34; A61B 17/3423; A61B 17/3498; A61B 17/02; A61B 17/0281
See application file for complete search history.

(56) References Cited

U.S. PATENT DOCUMENTS 5,368,545 A    11/1994    Schaller et al.
5,545,179 A *   8/1996    Williamson, IV .......... A61B 17/3423
                                                                          600/32
(Continued)

FOREIGN PATENT DOCUMENTS

CN    101617932 A    1/2010
CN    101999912 A    4/2011
(Continued)

OTHER PUBLICATIONS

International Search Report corresponding to Application No. PCT/CN2014/093840; dated Feb. 17, 2015, with English translation.

*Primary Examiner* — Christopher Beccia
(74) *Attorney, Agent, or Firm* — Cantor Colburn LLP

(57) ABSTRACT

A hollow celiac minimally invasive surgery endoscopic channel may include an extracorporeal combined platform and an intracorporeal expandable shell body. The combined platform and the intracorporeal expandable shell body may be engagingly combined into a detachable structure. The intracorporeal expandable shell body may be in a triangular frustum shape. A portion of the intracorporeal expandable shell body that is located below the triangular frustum surface may be a two-layer structure body. Partition stiffeners that are distributed horizontally may be provided between an inner and outer layers at each face of the shell body. An inflation port may be disposed at the inner layer.

9 Claims, 3 Drawing Sheets

(52) U.S. Cl.
CPC ... *A61B 17/3498* (2013.01); *A61B 2017/00557* (2013.01); *A61B 2017/00942* (2013.01); *A61B 2017/0225* (2013.01); *A61B 2017/3486* (2013.01)

(56) References Cited

U.S. PATENT DOCUMENTS

| | | | | |
|---|---|---|---|---|
| 5,653,705 | A | * | 8/1997 | de la Torre ........ A61B 17/3423 606/1 |
| 6,902,569 | B2 | * | 6/2005 | Parmer ................ A61B 90/11 606/108 |
| 2010/0261974 | A1 | * | 10/2010 | Shelton, IV ....... A61B 17/3423 600/208 |
| 2012/0095297 | A1 | * | 4/2012 | Dang ................ A61B 17/0218 600/208 |

FOREIGN PATENT DOCUMENTS

| | | |
|---|---|---|
| CN | 102805606 A | 12/2012 |
| CN | 103006296 A | 4/2013 |
| CN | 103654887 A | 3/2014 |
| CN | 203597984 U | 5/2014 |
| EP | 0754432 A1 | 1/1997 |

\* cited by examiner

HOLLOW CELIAC MINIMALLY INVASIVE SURGERY ENDOSCOPIC CHANNEL

CROSS REFERENCE TO RELATED APPLICATIONS

This is the U.S. national stage of application No. PCT/CN2014/093840, filed on Dec. 15, 2014. Priority under 35 U.S.C. § 119(a) and 35 U.S.C. § 365(b) is claimed from Chinese Application No. 201310699778.1, filed Dec. 18, 2013; the disclosure of which is incorporated herein by reference.

FIELD OF THE INVENTION

At least an embodiment of invention relates to an auxiliary instrument for celiac surgery, in particular, to a hollow celiac minimally invasive surgery endoscopic channel.

BACKGROUND

With the development of medical technology, a minimally invasive surgery using a celiac endoscopic technology has been increasingly promoted and used domestically. In a celiac endoscopic surgery, a 2-4 hole operation method is commonly used, wherein one hole is provided at the navel of human body (or other portions of the belly) for avoiding leaving a strip like scar at the celiac portion of the patient. After recovery, only 1 to 3 filiform scars each having a length of 0.5-1 cm will be left in the celiac portion. Such a surgery can be described as having smaller surface of wound and less pain. Therefore, some people call it "keyhole" operation. The implementation of celiac endoscopic surgery alleviates pain of the patient during the operation, and meanwhile, the recovery period of the patient is shortened and the expense of the patient is relatively decreased, making it become a fast developing operation program in recent years.

At the very beginning, both domestic and foreign hospitals use a single-hole or multiple-hole celiac endoscopic technology to perform a transumbilical single-hole endoscopic cholecystotomy, appendectomy, intrahepatic biliary cystadenoma, etc. During the operation, a celiac channel must be provided in the small cutouts having a diameter of 5-12 millimeters located at different portions of the belly for facilitating insertion of cameras and various special surgery operative instruments. The images of individual visceral organs in the abdominal cavity captured by the cameras inserted into the abdominal cavity are transmitted to the television screen for observation by surgeons so that various operative instruments can be operated extracorporeal to complete the operation.

However, a currently common minimally invasive surgery performed via a celiac channel having a small cutout shape in the belly has some obvious defects: after the small cutout is opened, under the action of internal pressure of the abdomen cavity, the visceral organs in the cavity will be pressed towards the cavity opening, thus resulting in such phenomenon as tissues and organs without pathological changes being injured accidentally by operative instruments. While currently a celiac channel conduit can be used to avoid such phenomenon, the currently used celiac channel conduit is overly simple, which means that not only it can not be located in the small cutout reliably under the action of the muscle of the belly of human body, but also it can not meet requirements of simultaneous operations of multiple apertures and multiple instruments.

Therefore, how to make the expansion of small cutout of the belly stable while still meeting the requirement of inserting multiple instruments from the same cutout has become a problem that needs to be addressed in the clinical minimally invasive operation.

Chinese patent documents have disclosed some technical solutions of single-hole or multiple-hole celiac endoscopic channel especially for use into abdomen cavity of human body via the belly. However, since all of these above proposed technical solutions use a columnar or a column like endoscopic channel as an expanded cavity body which is used as the celiac space for the minimally invasive operation, the following problem commonly exists after the endoscopic channel enters the abdomen cavity of human body: since the visceral organs in the abdomen cavity of human body are in a closely and orderly arranged state with each other and there might be a creepage relative to each other within a certain range, the column like endoscopic channel lacks a effective supportive point due to its columnar shape after entering the abdomen cavity of human body, thus lacking stability in the abdomen cavity; meanwhile, during the operation, once it is required for the channel to be displaced appropriately, a phenomenon that the channel sways randomly would become more common, thus making it unable to be promoted and used in clinical operation.

SUMMARY

At least an embodiment of the invention provides a hollow celiac minimally invasive surgery endoscopic channel, in hope that it can conveniently enter the abdomen cavity via a small cutout in the surface of abdomen cavity while also having a certain anti-external pressure function after entering the abdomen cavity, and can be simultaneously stably fixed at the operative position using the clearances among the visceral organs.

This type of hollow celiac minimally invasive surgery endoscopic channel comprise an extracorporeal combined platform 5 and an intracorporeal expandable shell body 6, wherein the combined platform 5 and the intracorporeal expandable shell body 6 are engagingly combined into a detachable structure, characterized in that the intracorporeal expandable shell body 6 is in a triangular frustum shape, and a portion of the intracorporeal expandable shell body that is located below the triangular frustum surface is a two-layer structure body, partition stiffeners 7 that are distributed horizontally are provided between an inner and outer layers at each face of the shell body, and an inflation port 9 is disposed at the inner layer, thus forming an overall inflation and deflation structure.

An upper portion of the intracorporeal expandable shell body 6 is a pyramid constituted by connecting three triangles with each other, and a lower portion of the intracorporeal expandable shell body 6 is a hollow triangular prism enclosing and extending vertically and downwardly from the bottom sides of three triangles.

The length of each bottom side of the intracorporeal expandable shell body 6 is 3-20 cm, and the height of the intracorporeal expandable shell body 6 is 3-20 cm.

The combined platform 5 is provided at least with an inflation tube entry passage 1, a conduit entry passage and several apparatus entry passages.

In the hollow celiac minimally invasive surgery endoscopic channel according to the above technical solution, the intracorporeal expandable shell body of the endoscopic channel is designed as a triangular prism, and a horizontal strip like air bag combination is formed on the columnar surface of the two-layer shell body by the partition stiffeners that are horizontally disposed. In this way, the three sides of the triangular prism can function to stabilize surrounding visceral organs in the abdomen cavity, and meanwhile, the stability of the triangular air bag body formed by the horizontal strip like air bags formed on the vertical surface of the intracorporeal expandable shell body can be made full use of, thus resisting a lateral pressure from the surrounding visceral organs in the abdomen cavity and ensuring there is a sufficient minimally invasive surgery space in the intracorporeal expandable shell body.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE UTILITY MODEL

At least an embodiment of the invention will be further described hereinafter with reference to the accompanying drawings, and embodiments of the invention will be given below.

Figure 1:
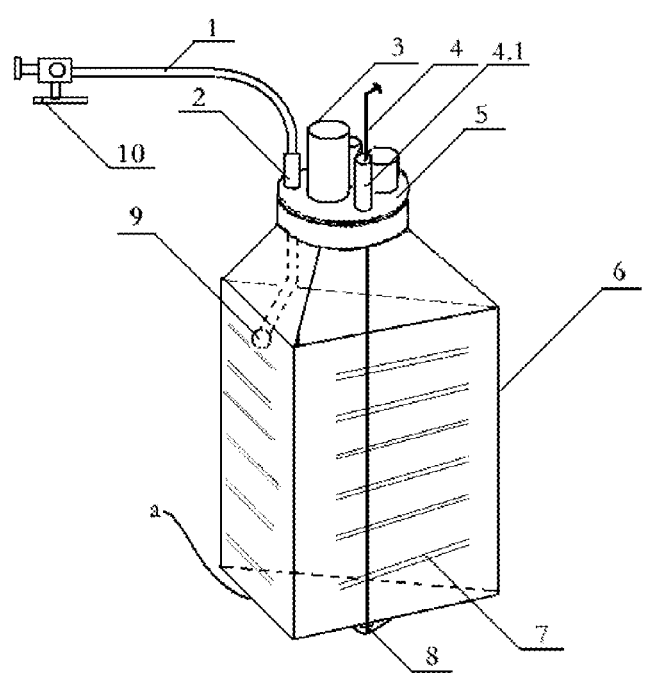
FIG. 1 is a schematic view showing an overall structure of at least an embodiment of the invention.
Figure 2:
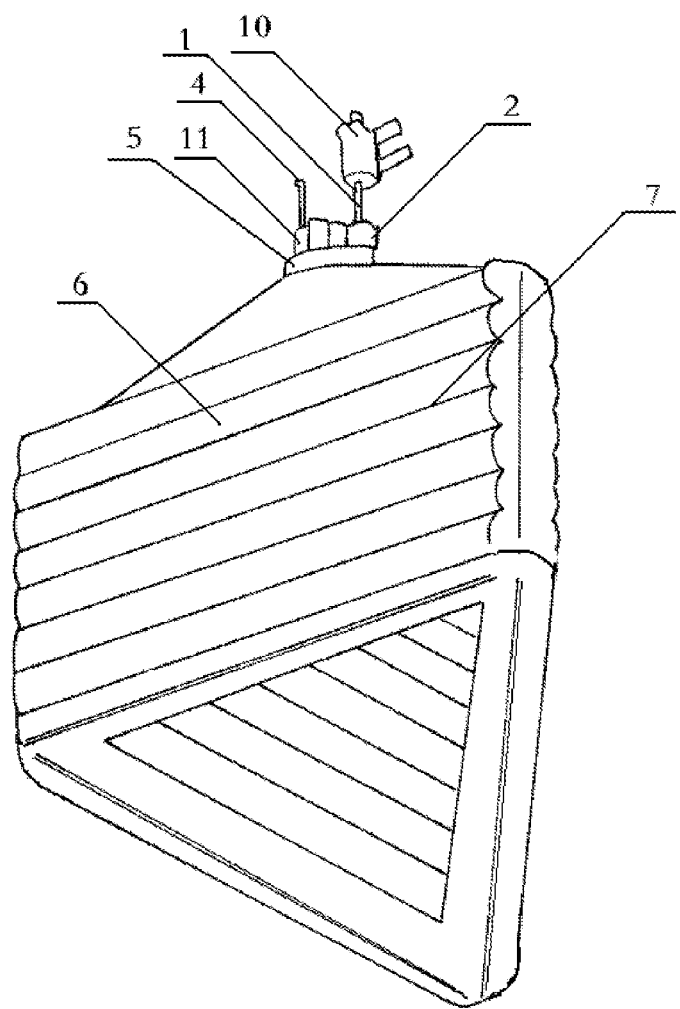
FIG. 2 is a schematic view showing an inflated state of at least an embodiment of the invention.

The hollow celiac minimally invasive surgery endoscopic channel as shown in FIGS. 1 to 2 is an innovative improvement on various celiac minimally invasive surgery endoscopic channels of relevant technical solutions that are currently used or not yet used but disclosed.

The type of hollow celiac minimally invasive surgery endoscopic channel comprises an extracorporeal combined platform 5 and an intracorporeal expandable shell body 6, wherein the combined platform 5 and the intracorporeal expandable shell body 6 are combined into a detachable structure, characterized in that the intracorporeal expandable shell body 6 is in a triangular frustum shape, a portion of the intracorporeal expandable shell body that is located below the triangular frustum surface is a two-layer structure body, partition stiffeners 7 that are distributed horizontally are provided between an inner and outer layers at each face of the shell body, and an inflation port 9 is disposed at the inner layer, thus forming an overall inflation and deflation structure.

An upper portion of the intracorporeal expandable shell body 6 is a pyramid constituted by connecting three triangles with each other, and a lower portion of the intracorporeal expandable shell body 6 is a hollow triangular prism enclosing and extending vertically and downwardly from the bottom sides of three triangles.

The length of each bottom side of the intracorporeal expandable shell body 6 is 3-20 cm, and the height of the intracorporeal expandable shell body 6 is 3-20 cm. Intracorporeal expandable shell bodies 6 having different heights can be selected according to different requirements on the operative positions so as to meet the requirement that the insertion depth of the operation control device can just reach the operation position and create a good operative view.

The combined platform 5 is provided at least with an inflation tube entry passage 2, a conduit entry passage and several apparatus entry passages 3.

The inflation tube entry passage 2 is provided therein with an inflation tube 1 which is a hollow tube having an outer diameter of 2 mm. A lower end of the inflation tube 1 extends into the intracorporeal expandable shell body 6 and is connected to an inflation port 9 provided at an inner layer of the intracorporeal expandable shell body 6. An outer end of the inflation tube 1 is provided with a control valve 10 mainly used for the inflation and expandable of the single-hole pneumoperitoneum-free device intracorporeal expandable shell body 6 as well as deflation of the intracorporeal expandable shell body 6 so that it can be removed from the body after the operation is completed.

The conduit entry passage 4.1 is provided therein with a conduit 4 which forms a detachable structure together with a guide rod connector 8 provided at a bottom side of the intracorporeal expandable shell body 6. The conduit 4 is mainly responsible for facilitating entry of the rolled intracorporeal expandable shell body 6 into a small cutout of the opened belly and moving the intracorporeal expandable shell body 6 that is already in the abdomen cavity to the operation position in the abdomen cavity so as to perform guiding; meanwhile, the conduit 4 can be also used for facilitating removal after operation. In practical use, a plurality of conduit mechanisms can be provided as required for operation.

In addition, in the hollow celiac minimally invasive surgery endoscopic channel provided by at least an embodiment of the invention, the passages on the multiple-hole platform 5 can be arranged according to different requirements of operation. Generally, five circular holes can be provided at an upper portion of the multiple-hole platform 5, wherein one hole has a diameter of 10 mm, two of 5 mm, and two of 2 mm. The five circular holes are mainly used for entry of operative instruments, entry of the inflation tube, and entry and exit of the reversing rod. Certain clearances are provided among the five holes so as to prevent the surgeon's operation from being affected by instruments that may cross each other.

In practical use, the surface of an outer film of the intracorporeal expandable shell body 6 is painted with a hydrophilic coating, and an outer surface of the intracorporeal expandable shell body 6 is painted with a hydrophilic coating. The hydrophilic coating is one of polyvinylpyrrolidone, polyoxyethylene, Polyethylene glycol, Polypropylene glycol, polyacrylamide and polyacrylate or a composite of them. The use of hydrophilic coating can reduce the resistance of the abdomen cavity channel in the operative cutout.

The hollow celiac minimally invasive surgery endoscopic channel provided by at least an embodiment of the invention has a small structure and can be conveniently operated. The pre-contracted shell body creates a therapy channel after entering human body via the small cutout and being inflated and expanded, and it can directly reach the focus.

In use, the intracorporeal expandable shell body 6 can be pre-contracted, and after entering the abdomen of human body via the operative minimally invasive cutout, it can be inflated and expanded so as to open a hollow operative channel which can directly reach the focus. By wedging the triangular frustum shape formed by the inflated intracorporeal expandable shell body 6 into the joining positions of various adjacent visceral organs in the abdomen cavity, an overall stability is ensured. Meanwhile, the multiple layers of horizontal triangular air bags in the inflated intracorporeal expandable shell body 6 enables the periphery of the whole inflated intracorporeal expandable shell body 6 to have a corresponding anti-pressure function. It is ensured that the inflated intracorporeal expandable shell body 6 has an enough space in the interior formed therein. Surgeons can insert a plurality of instruments via the five openings on the multiple-hole rear platform and operate them simultaneously with minimal influence on each other. This depends mainly on the distance between individual holes in the rear platform. For example, a laparoscope, a nipper, a separation scissors, an electrotome, a super knife or the like can be used to perform a belly surgery.

Figure 3:
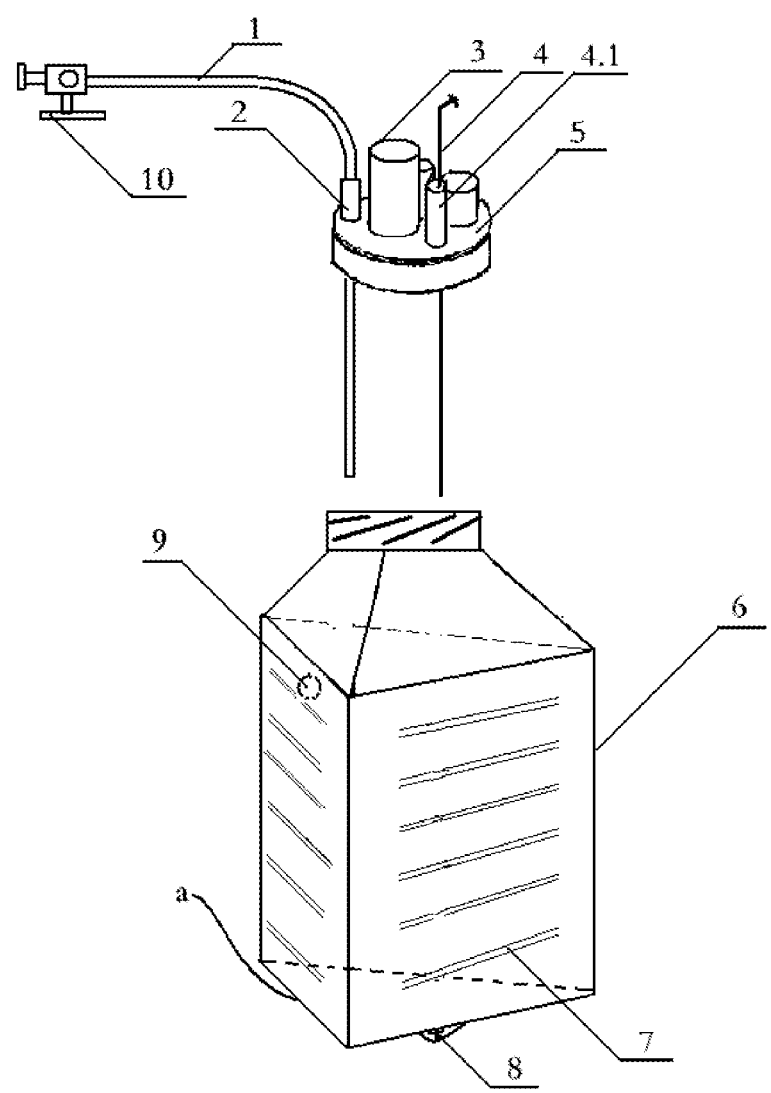
FIG. 3 is a schematic view showing a state in which the multiple-hole platform is detached from the intracorporeal expandable shell body.

In a clinical operation of minimally invasive surgery, once it is required to remove relevant tissues cut down during the operation, the multiple-hole platform 5 and the intracorporeal expandable shell body 6 can be detached so as to come into the state shown in FIG. 3. The tissues can be taken out via the upper openings in the intracorporeal expandable shell body 6 by using relevant operative instruments. The operation can be continued after installing the multiple-hole platform 5 onto the intracorporeal expandable shell body 6.

The hollow celiac minimally invasive surgery endoscopic channel of at least an embodiment of the invention can be widely used in transumbilical single-hole endoscopic cholecystotomy, appendectomy, gastrostomy, lienectomy, totally Extraperitoneal Prosthetic, prostatectomy, epinephroectomy, orchidorrhaphy, orchiectomy, ureterolithotomy, nephrectomy, pyeloplasty, etc.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

The invention claimed is:

1. A hollow celiac minimally invasive surgery endoscopic channel for use on a patient having visceral organs, the hollow celiac minimally invasive surgery endoscopic channel comprising:
    an extracorporeal combined platform and
    an intracorporeal expandable shell body;
    wherein the combined platform and the intracorporeal expandable shell body are engagingly combined into a detachable structure,
    an upper portion of the intracorporeal expandable shell body is in a triangular frustum shape,
    a portion of the intracorporeal expandable shell body that is located below the triangular frustum surface is a two-layer structure body,
    partition stiffeners that are distributed horizontally are provided between an inner and outer layers at each face of the shell body,
    and an inflation port is disposed at the inner layer.

2. A hollow celiac minimally invasive surgery endoscopic channel according to claim 1, wherein an upper portion of the intracorporeal expandable shell body is a pyramid comprising three triangles connected with each other, and a lower portion of the intracorporeal expandable shell body is a hollow triangular prism enclosing and extending vertically and downwardly from the bottom sides of the three triangles.

3. A hollow celiac minimally invasive surgery endoscopic channel according to claim 1, wherein a length of each bottom side of the intracorporeal expandable shell body is 3-20 cm, and the height of the intracorporeal expandable shell body (6) is 3-20 cm.

4. A hollow celiac minimally invasive surgery endoscopic channel according to claim 1, wherein the combined platform comprises an inflation tube entry passage, a conduit entry passage and a plurality of apparatus entry passages.

5. A hollow celiac minimally invasive surgery endoscopic channel according to claim 4, wherein the inflation tube entry passage comprises an inflation tube, an inner end of the inflation tube extends into the intracorporeal expandable shell body and is connected to an inflation port provided at an inner layer of the intracorporeal expandable shell body, and an outer end of the inflation tube is provided with a control valve.

6. A hollow celiac minimally invasive surgery endoscopic channel according to claim 4, wherein the conduit entry passage comprises a conduit which forms a detachable structure together with a guide rod connector provided at a bottom side of the intracorporeal expandable shell body.

7. A hollow celiac minimally invasive surgery endoscopic channel according to claim 1, wherein an outer surface of the intracorporeal expandable shell body is painted with a hydrophilic coating, and the hydrophilic coating is one of polyvinylpyrrolidone, polyoxyethylene, Polyethylene glycol, Polypropylene glycol, polyacrylamide and polyacrylate or a composite thereof.

8. A hollow celiac minimally invasive surgery endoscopic channel according to claim 1, wherein a lower portion of the intracorporeal expandable shell is a hollow triangular prism shape; and
    the partition stiffeners are structured so as to maintain the hollow triangular prism shape of the lower portion of the intracorporeal expandable shell against pressure from the visceral organs of the patient.

9. A hollow celiac minimally invasive surgery endoscopic channel according to claim 1, wherein the intracorporeal expandable shell is structured to form an unsealed passage during surgery on the patient.

* * * * *